(12) United States Patent
Emrick et al.

(10) Patent No.: US 10,106,630 B2
(45) Date of Patent: Oct. 23, 2018

(54) UNSATURATED DEOXYBENZOIN COMPOUND, POLYMER PREPARED THEREFROM, AND ARTICLES COMPRISING THE POLYMER

(71) Applicant: The University of Massachusetts, Boston, MA (US)

(72) Inventors: Todd Emrick, South Deerfield, MA (US); E. Bryan Coughlin, Amherst, MA (US); Megan Szyndler, Wyandotte, MI (US); Aabid A. Mir, Rochester, NY (US); Justin C. Timmons, Lafayette Hill, PA (US)

(73) Assignee: THE UNIVERSITY OF MASSACHUSETTS, Boston, MA (US)

( * ) Notice: Subject to any disclaimer, the term of this patent is extended or adjusted under 35 U.S.C. 154(b) by 29 days.

(21) Appl. No.: 15/472,508

(22) Filed: Mar. 29, 2017

(65) Prior Publication Data
US 2017/0283355 A1    Oct. 5, 2017

Related U.S. Application Data (60) Provisional application No. 62/316,874, filed on Apr. 1, 2016.

(51) Int. Cl.
*C08F 36/22* (2006.01)
*C08F 36/20* (2006.01)
(Continued)

(52) U.S. Cl.
CPC .............. *C08F 36/22* (2013.01); *C07C 49/84* (2013.01); *C08F 12/34* (2013.01); *C08F 16/36* (2013.01);
(Continued)

(58) Field of Classification Search
CPC .......... C09K 21/06; C08F 36/20; C08F 36/22; C08F 136/20; C08F 136/22; C08F 236/20; C08F 236/22; C08F 16/36; C08F 116/36; C08F 216/36; C08F 12/34; C08F 112/34; C08F 212/34
See application file for complete search history.

(56) References Cited

U.S. PATENT DOCUMENTS 7,863,400 B2   1/2011   Emrick et al.
8,314,202 B2   11/2012  Emrick et al.
(Continued)

FOREIGN PATENT DOCUMENTS

JP    02273288 A   * 11/1990
JP    H02273288      11/1990

OTHER PUBLICATIONS

Ellzey et al., "Deoxybenzoin-Based Polyarylates as Halogen-Free Fire-Resistant Polymers" Macromolecules; 2006; 39; 3553-3558.
(Continued)

*Primary Examiner* — Ling Siu Choi
*Assistant Examiner* — David L Miller
(74) *Attorney, Agent, or Firm* — Cantor Colburn LLP (57) ABSTRACT

An unsaturated deoxybenzoin compound has the structure (I)

(Continued)

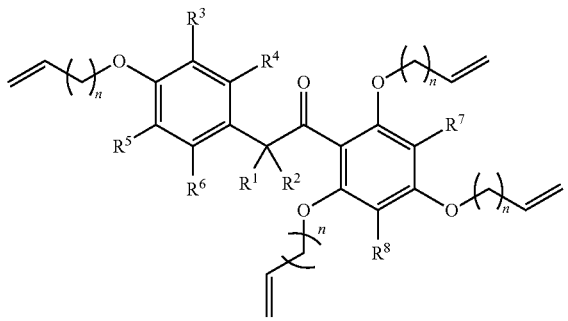

wherein $R^1$, $R^2$, $R^3$, $R^4$, $R^5$, $R^6$, $R^7$, $R^8$, and n are defined herein. A polymer including at least one group derived from a deoxybenzoin compound having structure (I), (II), or a combination thereof

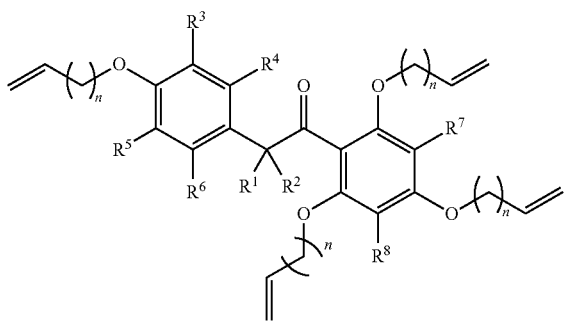

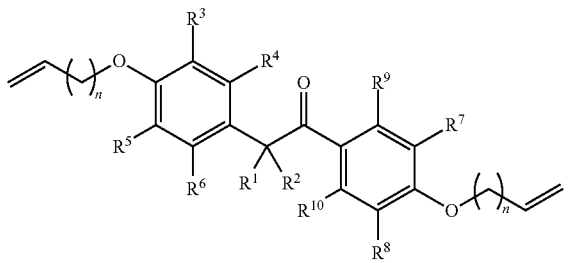

is also described, wherein $R^1$, $R^2$, $R^3$, $R^4$, $R^5$, $R^6$, $R^7$, $R^8$, $R^9$, $R^{10}$, and n are defined herein.

14 Claims, 2 Drawing Sheets

(51) Int. Cl.

| | | |
|---|---|---|
| C07C 49/84 | (2006.01) |
| C09K 21/06 | (2006.01) |
| C08F 136/20 | (2006.01) |
| C08F 236/20 | (2006.01) |
| C08F 16/36 | (2006.01) |
| C08F 212/34 | (2006.01) |
| C08F 236/22 | (2006.01) |
| C08F 116/36 | (2006.01) |
| C08F 112/34 | (2006.01) |
| C08F 136/22 | (2006.01) |
| C08F 12/34 | (2006.01) |
| C08F 216/36 | (2006.01) |
| C09K 21/14 | (2006.01) |

(52) U.S. Cl.
CPC ............ *C08F 36/20* (2013.01); *C08F 112/34* (2013.01); *C08F 116/36* (2013.01); *C08F 136/20* (2013.01); *C08F 136/22* (2013.01); *C08F 212/34* (2013.01); *C08F 216/36* (2013.01); *C08F 236/20* (2013.01); *C08F 236/22* (2013.01); *C09K 21/06* (2013.01); *C09K 21/14* (2013.01)

(56) References Cited

U.S. PATENT DOCUMENTS

| | | | |
|---|---|---|---|
| 2013/0102754 A1 | 4/2013 | Emrick et al. |
| 2014/0155569 A1 | 6/2014 | Kumar et al. |
| 2014/0357829 A1* | 12/2014 | Emrick ............ C08G 59/3218 528/87 |
| 2017/0101361 A1 | 4/2017 | Mir et al. |

OTHER PUBLICATIONS

Lyon et al., "Pyrolysis combustion flow calorimetry" J. Anal. Appl. Pyrolysis; 2004; 71; 27-46.

Walters et al., "Comparison of Heat Release Criterion for Noncombustible Materials" International SAMPE Symposium and Exhibition; 2005; 50; 1118.

* cited by examiner

UNSATURATED DEOXYBENZOIN COMPOUND, POLYMER PREPARED THEREFROM, AND ARTICLES COMPRISING THE POLYMER

BACKGROUND

Polymers are a mainstay of modern society, for example, widely used in fabricating textiles, upholstery, construction materials, various air, land or sea vehicles, and microelectronic devices and appliances. The inherent flammability of many polymers poses a significant threat, especially in enclosed or isolated spaces. Therefore, as synthetic polymers are used extensively in society as plastics, rubbers, and textiles, polymer flammability has been recognized as a safety hazard and remains an important challenge in polymer research.

Flame retardancy of polymers is often achieved by blending polymers with flame retardant additives, such as halocarbons, including polybrominated diphenyl ether (PBDE), phosphorus, organophosphates, and metal oxides. While small molecule flame retardant additives provide a convenient means for reducing flammability of polymers, these additives can compromise safety from environmental and health perspectives. Conventional flame retardants are small molecule additives that often leach out of the polymer during their use leading to a variety of serious health and environmental problems associated with toxicity and bioaccumulation. These concerns have led to an emphasis on non-halogenated flame retardants in recent years. However, non-halogenated flame retardant additives, such as alumina trihydrate, compromise the physical and mechanical properties of polymers when loaded at high levels.

An ideal low-flammable polymer would be halogen-free and possess high thermal stability, low heat of combustion, and a low combustion heat release rate (HRR), with minimal release of toxic fumes. Intrinsically fire-resistant polymers that undergo significant carbonization upon heating are highly desirable, as carbonaceous char formation effectively averts combustion by producing an insulating layer on the polymer surface. Such char formation can also be realized from composite materials in which an additive ultimately provides the desired char.

Deoxybenzoin moieties have demonstrated utility as flame retardant materials, for example when incorporated in polyarylates, e.g., polyarylates based on 4,4'-bishydroxydeoxybenzoin (BHDB), as a bisphenolic monomer. Such polymers exhibited low combustion heat release rate and total heat of combustion, which is believed to arise from the thermally-induced conversion of BHDB to diphenylacetylene moieties that char by aromatization. See, K. A. Ellzey, T. Ranganathan, J. Zilberman, E. B. Coughlin, R. J. Farris, T. Emrick, *Macromolecules* 2006, 39, 3553. Pyrolysis combustion flow calorimetry (PCFC), an oxygen consumption technique for measuring heat release capacity (HRC), revealed exceptionally low HRC values for the BHDB-polyarylates (<100 J/g-K). See, R. N. Walters, M. Smith, and M. R. Nyden, *International SAMPE Symposium and Exhibition* 2005, 50, 1118.

It would be advantageous to identify new synthetic methodologies for integrating deoxybenzoin moieties into polymeric materials. Accordingly, there remains a continuing need for synthetic strategies toward structurally and functionally diverse flame-retardant materials, including high molecular weight polymers and crosslinked materials.

BRIEF SUMMARY

One embodiment is an unsaturated deoxybenzoin compound having the structure (I)

wherein $R^1$ and $R^2$ are independently at each occurrence hydrogen, a halogen, a nitrile group, a $C_{1-6}$ alkyl group, a $C_{2-13}$ alkenyl group, a $C_{2-13}$ alkynyl group, a $C_{6-20}$ aryl group, a $C_{7-13}$ arylalkyl group, a $C_{7-13}$ alkylaryl group; $R^3$, $R^4$, $R^5$, $R^6$, $R^7$, and $R^8$ are independently at each occurrence hydrogen, a halogen, a hydroxyl group, a nitrile group, a $C_{1-6}$ alkyl group, a $C_{2-13}$ alkenyl group, a $C_{2-13}$ alkynyl group, a $C_{1-6}$ alkoxy group, a $C_{6-20}$ aryl group, a $C_{7-13}$ arylalkyl group, a $C_{7-13}$ alkylaryl group, or a $C_{4-12}$ cycloalkyl group; and n is independently at each occurrence an integer from 1 to 12.

Another embodiment is a polymer comprising at least one group derived from a deoxybenzoin compound having structure (I), (II), or a combination thereof wherein $R^1$ and $R^2$ are independently at each occurrence hydrogen, a halogen, a nitrile group, a $C_{1-6}$ alkyl group, a $C_{2-13}$ alkenyl group, a $C_{2-13}$ alkynyl group, a $C_{6-20}$ aryl group, a $C_{7-13}$ arylalkyl group, or a $C_{7-13}$ alkylaryl group; $R^3$, $R^4$, $R^5$, $R^6$, $R^7$, $R^8$, $R^9$, and $R^{10}$ are independently at each occurrence hydrogen, a halogen, a hydroxyl group, a nitrile group, a $C_{1-6}$ alkyl group, a $C_{2-13}$ alkenyl group, a $C_{2-13}$ alkynyl group, a $C_{1-6}$ alkoxy group, a $C_{6-20}$ aryl group, a $C_{7-13}$ arylalkyl group, a $C_{7-13}$ alkylaryl group, or a $C_{4-12}$ cycloalkyl group; and n is independently at each occurrence an integer from 1 to 12.

An article comprising the polymer is also described.

These and other embodiments are described in detail below.

BRIEF DESCRIPTION OF THE DRAWINGS

The following Figures are exemplary embodiments.

DETAILED DESCRIPTION

The present inventors have prepared new derivatives of deoxybenzoin containing unsaturation. In particular, the present inventors have prepared difunctional and tetrafunctional unsaturated deoxybenzoin derivatives, for example a diallyl-functionalized deoxybenzoin and a tetraallyl-functionalized deoxybenzoin. The unsaturated deoxybenzoin compounds described herein advantageously offer an opportunity for further functionalization, or incorporation into polymer materials, for example by copolymerization with one or more ethylenically unsaturated monomers or by crosslinking unsaturated polymers (e.g., polymers having in-chain unsaturation, unsaturated pendent groups, chain-end unsaturation, or a combination thereof). The deoxybenzoin compounds further exhibit exceptional thermal properties including heat release capacity, total heat release, peak heat released rate, and char yield. Thus, the deoxybenzoin derivatives described herein are expected to contribute to reduction of heat release upon burning of a material including these deoxybenzoin compounds.

Accordingly, one aspect of the present disclosure is an unsaturated deoxybenzoin compound having the structure (I)

(I)

wherein $R^1$ and $R^2$ are independently at each occurrence hydrogen, a halogen, a nitrile group, a $C_{1-6}$ alkyl group, a $C_{2-13}$ alkenyl group, a $C_{2-13}$ alkynyl group, a $C_{6-20}$ aryl group, a $C_{7-13}$ arylalkyl group, or a $C_{7-13}$ alkylaryl group; $R^3$, $R^4$, $R^5$, $R^6$, $R^7$, and $R^8$ are independently at each occurrence hydrogen, a halogen, a hydroxyl group, a nitrile group, a $C_{1-6}$ alkyl group, a $C_{2-13}$ alkenyl group, a $C_{2-13}$ alkynyl group, a $C_{1-6}$ alkoxy group, a $C_{6-20}$ aryl group, a $C_{7-13}$ arylalkyl group, a $C_{7-13}$ alkylaryl group, or a $C_{4-12}$ cycloalkyl group; and n is independently at each occurrence an integer from 1 to 12 (e.g., n is independently at each occurrence 1, 2, 3, 4, 5, 6, 7, 8, 9, 10, 11, or 12). In some embodiments, each occurrence of $R^1$ and $R^2$ is hydrogen. In some embodiments, each occurrence of n is 1. In some embodiments, each occurrence of $R^3$, $R^4$, $R^5$, $R^6$, $R^7$, and $R^8$ is hydrogen.

In a specific embodiment, the deoxybenzoin compound has the structure (I), wherein each occurrence of $R^1$ and $R^2$ is hydrogen, each occurrence of n is 1; and each occurrence of $R^3$, $R^4$, $R^5$, $R^6$, $R^7$, and $R^8$ is hydrogen. For example, the deoxybenzoin compound can have the structure (IA)

(IA)

In some embodiments, the unsaturated deoxybenzoin compound can exhibit one or more advantageous properties, for example one or more advantageous thermal properties. For example, the deoxybenzoin compound can exhibit a heat release capacity (HRC) of less than or equal to 250 joules per gram-Kelvin, for example greater than 0 to 250 joules per gram-Kelvin, for example 50 to 250 joules per gram-Kelvin, for example 100 to 250 joules per gram-Kelvin, for example 150 to 250 joules per gram-Kelvin, determined using a pyrolysis combustion flow calorimeter. Describing these systems in terms of HRC eliminates the reliance on heating rate that is typical of standard flammability measurements (i.e. heat release rate), rendering it a material dependent property. In some embodiments, the deoxybenzoin compound can exhibit a total heat release (THR) of less than 20 kilojoules per gram, for example greater than 0 to 20 kilojoules per gram, or 5 to 20 kilojoules per gram, or 10 to 20 kilojoules per gram, determined using a pyrolysis combustion flow calorimeter. THR is the total heat of complete combustion of the pyrolysis products per mass of sample used in the measurement. Lower HRC and THR values are thus good indicators of increasing the flame retarding property of the polymer. In some embodiments, the deoxybenzoin compound can exhibit a peak heat released rate (PHHR) of less than 200 W/g, for example 80 to 200 W/g, for example 100 to 200 W/g, determined using a pyrolysis combustion flow calorimeter. In some embodiments, the deoxybenzoin compound can exhibit a char yield of at least 10 percent, for example 10 to 50 percent, for example 10 to 40 percent, after 60 minutes at 750° C., as determined by thermogravimetric analysis. In some embodiments, the deoxybenzoin compound exhibits at least one of the foregoing thermal properties. In some embodiments, the deoxybenzoin compound exhibits at least two of the foregoing thermal properties. In some embodiments, the deoxybenzoin compound exhibits at least three of the foregoing thermal properties. In some embodiments, the deoxybenzoin compound exhibits each of the foregoing thermal properties.

Another aspect of the present disclosure is a polymer comprising at least one group derived from a deoxybenzoin compound having structure (I), (II), or a combination thereof

(I)

(II)

wherein $R^1$ and $R^2$ are independently at each occurrence hydrogen, a halogen, a nitrile group, a $C_{1-6}$ alkyl group, a $C_{2-13}$ alkenyl group, a $C_{2-13}$ alkynyl group, a $C_{6-20}$ aryl group, a $C_{7-13}$ arylalkyl group, or a $C_{7-13}$ alkylaryl group; $R^3$, $R^4$, $R^5$, $R^6$, $R^7$, $R^8$, $R^9$, and $R^{10}$ are independently at each occurrence hydrogen, a halogen, a hydroxyl group, a nitrile group, a $C_{1-6}$ alkyl group, a $C_{2-13}$ alkenyl group, a $C_{2-13}$ alkynyl group, a $C_{1-6}$ alkoxy group, a $C_{6-20}$ aryl group, a $C_{7-13}$ arylalkyl group, a $C_{7-13}$ alkylaryl group, or a $C_{4-12}$ cycloalkyl group; and n is independently at each occurrence an integer from 1 to 12 (e.g., n is independently at each occurrence 1, 2, 3, 4, 5, 6, 7, 8, 9, 10, 11, or 12). In some embodiments, each occurrence of $R^1$ and $R^2$ is hydrogen. In some embodiments, each occurrence of n is 1. In some embodiments, each occurrence of $R^3$, $R^4$, $R^5$, $R^6$, $R^7$, $R^8$, $R^9$, and $R^{10}$ is hydrogen.

In some embodiments, the polymer includes at least one group derived from the deoxybenzoin compound having structure (I)

(I)

wherein each of $R^1$, $R^2$, $R^3$, $R^4$, $R^5$, $R^6$, $R^7$, $R^8$, and n are as described above. In a specific embodiment, the polymer includes at least one group derived from the deoxybenzoin compound having structure (IA)

(IA)

In some embodiments, the polymer includes at least one group derived from the deoxybenzoin compound having structure (II)

(II)

wherein each of $R^1$, $R^2$, $R^3$, $R^4$, $R^5$, $R^6$, $R^7$, $R^8$, $R^9$, $R^{10}$, and n are as described above. In a specific embodiment, the polymer includes at least one group derived from the deoxybenzoin compound having structure (IIA)

(IIA)

In some embodiments, the polymer includes at least one group derived from the deoxybenzoin compound having structure (I) and at least one group derived from the deoxybenzoin compound having structure (II). In some embodiments, the deoxybenzoin compound having structure (I) and the deoxybenzoin compound having structure (II) can be present in the polymer in a weight ratio of 1:99 to 99:1.

As used herein, "at least one group derived from a deoxybenzoin compound having structure (I), (II), or a combination thereof" means that the polymer includes at least one group or residue having structure (IB) or (IIB)

wherein the curved lines indicate the points of attachment of the deoxybenzoin compound to the polymer, and each of $R^1$, $R^2$, $R^3$, $R^4$, $R^5$, $R^6$, $R^7$, $R^8$, $R^9$, $R^{10}$, and n are as described above. In some embodiments, the polymer comprises at least one group according to structure (IB). In some embodiments, the polymer comprises at least one group according to structure (IIB). In some embodiments, the polymer comprises at least one of structure (IB) and at least one of structure (IIB).

In some embodiments, the polymer consists of repeating units derived from a deoxybenzoin compound having structure (I), (II), or a combination thereof. Stated another way, in some embodiments, the polymer excludes any groups or repeating units derived from any monomer other than the deoxybenzoin compound having structure (I) or (II).

In some embodiments, the polymer can be derived from the deoxybenzoin compound having structure (I), (II), or a combination thereof, and one or more ethylenically unsaturated monomers. Stated another way, the polymer can further include repeating units derived from an ethylenically unsaturated monomer. Exemplary ethylenically unsaturated monomers can include, but are not limited to, styrenic monomers, $C_{1-12}$ alkyl (meth)acrylate monomers, $C_{6-20}$ aryl (meth)acrylate monomers, (meth)acrylic acid, (meth)acrylamides, alpha olefins, vinyl esters, vinyl alkyl ethers, alkylene oxide (meth)acrylates, oligoalkylene oxide (meth)acrylates (e.g., triethylene glycol methacrylate, tetraethylene glycol methacrylate, polyethylene glycol methacrylates, and the like), unsaturated nitrile-containing monomers (e.g., acrylonitrile, and the like) or a combination thereof. Specific examples of suitable ethylenically unsaturated monomers can include styrene, alpha-methylstyrene, vinyl toluene, acrylic acid, methacrylic acid, methyl methacrylate, triethylene glycol methacrylate, tetraethylene glycol methacrylate, acrylonitrile, vinyl acetate, allyl acetate, acrylamide, acrylonitrile, or a combination thereof.

The polymer derived from the deoxybenzoin compound and an ethylenically unsaturated monomer can be prepared by any suitable method that is generally known for polymerizing ethylenically unsaturated monomers. For example, the deoxybenzoin compound and the ethylenically unsaturated monomer can be mixed in the desired amounts, optionally in the presence of a solvent effective to dissolve the reaction components. When present, the solvent is preferably a non-reactive solvent. The deoxybenzoin compound and the ethylenically unsaturated monomer can be reacted under conditions effective to provide the desired polymer. For example, the reaction can be carried out in the presence of light, heat, acid, a metal catalyst (e.g., a transition metal catalyst comprising, for example, ruthenium, molybdenum, or tungsten), a radical-generating species (e.g., a photoinitiator or a thermal initiator), or any suitable combination thereof to effect a reaction between the deoxybenzoin compound and the ethylenically unsaturated monomer.

When present, the polymer can include the ethylenically unsaturated monomer in an amount of 1 to 99 weight percent, based on the total weight of the polymer. The content of the polymer can be determined using, for example, nuclear magnetic resonance (NMR) spectroscopy.

In some embodiments, the polymer can be derived from a polymer having in-chain unsaturation and the deoxybenzoin compound having structure (I), (II), or a combination thereof. In some embodiments, the polymer having in-chain unsaturation can be an unsaturated polyolefin, an unsaturated aliphatic polyester, an unsaturated elastomer, an unsaturated aliphatic polyurethane, or a combination thereof, preferably an unsaturated polyolefin, an unsaturated aliphatic polyester, an unsaturated elastomer, or a combination thereof. The degree of in-chain aliphatic unsaturation can be evaluated by a variety of methods, for example infrared spectroscopy and $^1H$ and $^{13}C$ nuclear magnetic resonance spectroscopy. The polymer having in-chain unsaturation preferably has at least 1% in-chain aliphatic unsaturation, or at least 5% in-chain aliphatic unsaturation, or at least 10% in chain aliphatic unsaturation, based on the total number of repeating units. In some embodiments, each repeating unit has in-chain unsaturation.

In some embodiments, the polymer having in-chain unsaturation is an unsaturated polyolefin. The unsaturated polyolefin can be, for example, polybutadiene, poly(cyclooctene), poly(norbornene), polyacetylene, poly(dicyclopentadiene), poly(maleic anhydride) and copolymers thereof, and the like, and copolymers thereof. In some embodiments, the polymer having in-chain unsaturation can be an unsaturated aliphatic polyester, for example a polyester comprising repeating units derived from maleic acid, fumaric acid, aconitic acid, mesaconic acid, citraconic acid, itaconic acid, a substituted derivative thereof, or a reactive derivative thereof (e.g., the corresponding anhydride or acid halide). In some embodiments, the polymer having in-chain unsaturation can be an unsaturated elastomer. Examples of unsaturated elastomers can include natural polyisoprene rubber, a synthetic polyisoprene rubber, a homopolymer of 1,3-butadiene, 2-methyl-1,3-butadiene, 1,3-pentadiene, 2-chloro-1,3 butadiene, or 2,3-dimethyl-1,3-butadiene, a copolymer of 1,3-butadiene, 2-methyl-1,3-butadiene, 1,3-pentadiene, 2-chloro-1,3 butadiene, or 2,3-dimethyl-1,3-butadiene with styrene, alpha-methylstyrene, acrylonitrile, isoprene, methacrylonitrile, methyl acrylate, ethyl acrylate, methyl methacrylate, ethyl methacrylate, or vinyl acetate, ethylene-vinyl acetate, chloroprene rubber, butyl rubber, halogenated butyl rubber, nitrile rubber, hydrogenated nitrile rubber, ethylene-propylene rubber, ethylene-propylene-diene rubber, unsaturated silicone rubber, or a combination thereof. Specific elastomers include polybutadiene rubber, poly(acrylonitrile-butadiene), poly(styrene-butadiene) rubber, polyisoprene rubber, neoprene rubber, or a combination thereof.

The polymer can be prepared by mixing the deoxybenzoin compound and the polymer having in-chain unsaturation to form a prepolymer mixture. The desired polymer can be provided upon reacting the polymer having in-chain unsaturation with the deoxybenzoin compound, for example using light, heat, acid, a metal catalyst (e.g., a transition metal catalyst comprising, for example, ruthenium, molybdenum, or tungsten), a radical-generating species (e.g., a photoinitiator or a thermal initiator), or any suitable combination thereof to effect a reaction between the deoxybenzoin compound and the in-chain unsaturation.

In some embodiments, the polymer is derived from the deoxybenzoin compound having structure (I), (II), or a combination thereof, and a polymer having one or more unsaturated pendent groups, one or more unsaturated end-groups, or both. For example, the polymer can be a macromeric (meth)acrylate. Macromeric (meth)acrylates can be (meth)acrylate-terminated oligomers or polymers, and can include, for example, (meth)acrylate-terminated styrene oligomers or polymers, (meth)acrylate-terminated polyethers (e.g., oligoethylene glycol (meth)acrylates). The "macromeric (meth)acrylates" are generally understood to be oligomers or polymers having at least one (meth)acrylate end-group. In some embodiments, the macromeric (meth)acrylates comprise at least two (meth)acrylate end-groups. In some embodiments, macromeric (meth)acrylates can be multifunctional (meth)acrylates, for example, having greater than two (meth)acrylate functional groups present, preferably as end-groups. In some embodiments, the macromeric (meth)acrylates can be (meth)acrylate-terminated polymers having a molecular weight of, for example, at least 500 grams per mole, or 500 to 50,000 grams per mole, or 500 to 10,000 grams per mole. In some embodiments, the macromeric (meth)acrylates can be (meth)acrylate-terminated oligomers, having a molecular weight of, for example, less than or equal to 1,000 Da. Thus, the polymer can be provided by reacting the polymer having one or more unsaturated pendent groups, one or more unsaturated end-groups, or both, with the deoxybenzoin compound. For example, the reaction can be carried out in the presence of light, heat, acid, a metal catalyst, a radical-generating species, or any suitable combination thereof to effect the desired reaction.

As described above, the polymer can be prepared by reacting the deoxybenzoin compound with any monomer or polymer that has unsaturation. The unsaturation can be present in the backbone of the polymer chain, as pendent groups along the polymer chain, or as chain-ends of a polymer.

In some embodiments, the final polymer has a molecular weight of 10,000 to 500,000 grams per mole, as determined by gel permeation chromatography.

In some embodiments, the final polymer can be at least partially crosslinked. For example, the polymer can be crosslinked by the deoxybenzoin compound having structure (I), (II), or a combination thereof.

In some embodiments, the group or residue derived from the deoxybenzoin compound can be present in the final polymer in an amount of 0.1 to 100 weight percent, or 1 to 99 weight percent, or 1 to 90 weight percent, or 1 to 75 weight percent of 1 to 50 weight percent, or 1 to 35 weight percent or 10 to 25 weight percent, based on the total weight of the final polymer.

In some embodiments, the polymer can exhibit one or more advantageous thermal properties. For example, the polymer can exhibit a heat release capacity (HRC) of less than or equal to 250 joules per gram-Kelvin, for example 150 to 250 joules per gram-Kelvin, determined using a pyrolysis combustion flow calorimeter. In some embodiments, the polymer can exhibit a total heat release (THR) of less than 20 kilojoules per gram, for example 10 to 20 kilojoules per gram, determined using a pyrolysis combustion flow calorimeter. In some embodiments, the polymer can exhibit a char yield of at least 30 percent, for example 30 to 50 percent, after 60 minutes at 750° C., as determined by thermogravimetric analysis. In some embodiments, the polymer exhibits at least two of the foregoing thermal properties. In some embodiments, the polymer exhibits at least three of the foregoing thermal properties. In some embodiments, the polymer exhibits each of the foregoing thermal properties.

The compounds and polymers and the synthetic methodologies disclosed herein can have broad impact on such diverse fields of fabricating textiles, upholstery, construction materials, various air, land or sea vehicles, and microelectronic devices and appliances. Thus the deoxybenzoin compounds and polymers prepared therefrom as described above can be particularly useful for the manufacture of various articles, specifically where improved thermal properties or flame retardance is desired. In some embodiments, the article can be a film, a coating (e.g., a UV-curable coating), a fiber, a textile, a furniture component, construction materials (e.g., insulation), a vehicle component (e.g., an automobile component, a railway vehicle component, a marine vehicle component, an airplane component, and the like), an electronic component, an adhesive, or a foam.

The deoxybenzoin compounds and polymers prepared therefrom are further illustrated by the following non-limiting examples.

EXAMPLES

Experimental details for the synthesis of allyl-functionalized deoxybenzoin are provided below.

Figure 1:
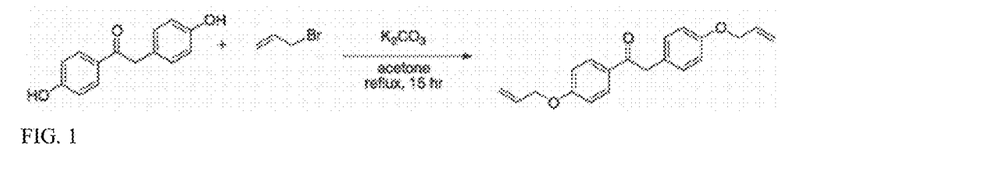
FIG. 1 is a reaction scheme showing the synthesis of diallyl-functionalized deoxybenzoin.

The diallyl ether of 4,4'-bishydroxydeoxybenzoin (BHDB), shown in FIG. 1, was prepared according to the following procedure. BHDB (25 grams, 110 millimoles), shown as compound 1 of FIG. 1, was dissolved in acetone (1 liter). Potassium carbonate (42.6 grams, 307 millimoles) was added, followed by allyl bromide (20 milliliters). The solution was heated to reflux for 12 hours, then allowed to cool to room temperature. Water (about 1 liter) was added until a precipitate formed. This solid product was filtered, dried, and recrystallized from methanol to yield off-white crystals (melting point: 83-85° C.); Proton nuclear magnetic resonance ($^1$H-NMR) spectrum (CDCl$_3$, 500 megahertz (MHz)): δ 7.91 (2H, d, J=9, Ar—H); 7.10 (2H, d, J=8.5, Ar—H); 6.87 (2H, d, J=9, Ar—H); 6.80 (2H, d, J=8.5, Ar—H); 5.96 (2H, m, CH=CH$_2$); 5.36 (2H, m, CH$_2$=CH); 5.25 (2H, m, CH$_2$=CH); 4.52 (2H, d, J=5); 4.43 (2H, d, J=5.5); 4.09 (2H, s, Ar—CO—CH$_2$—Ar). $^{13}$Carbon ($^{13}$C) NMR spectrum (CDCl$_3$, 500 megahertz (MHz)): δ 196.63, 162.68, 157.65, 133.48, 132.67, 131.04, 129.95, 127.24, 118.27, 117.24, 115.01, 68.98 (O—*CH$_2$—CH=CH$_2$), 44.54.

Figure 2:
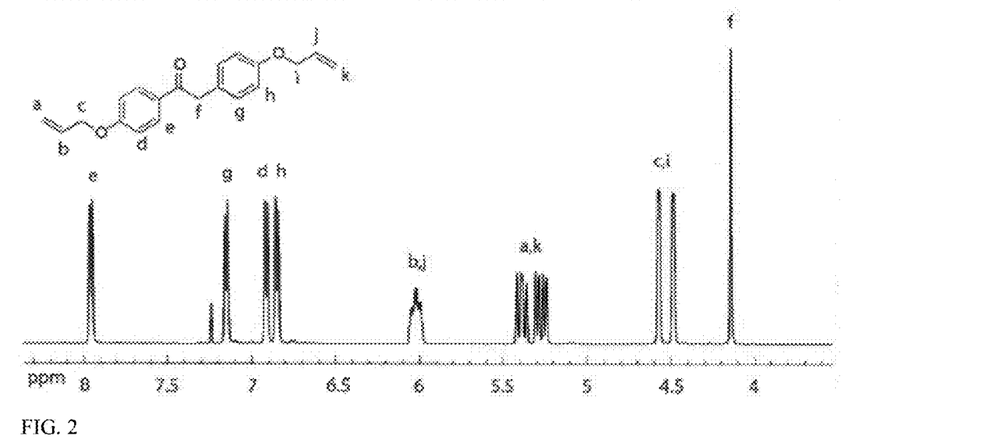
FIG. 2 is a proton nuclear magnetic resonance ($^1$H NMR) spectrum of diallyl-functionalized deoxybenzoin.

The $^1$H NMR spectrum of the diallyl ether of BHDB is shown in FIG. 2.

Figure 3:
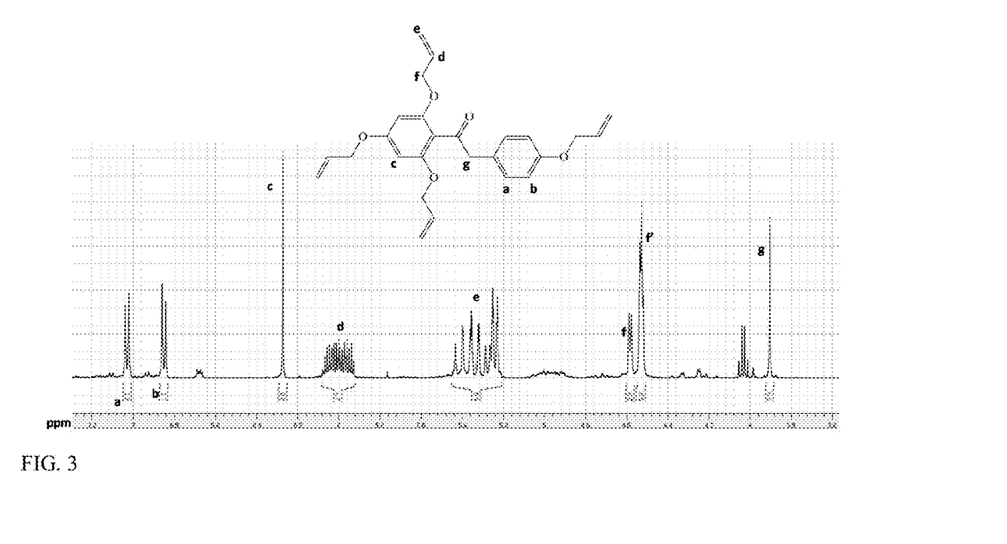
FIG. 3 is $^1$H NMR spectrum of tetra-allyl-functionalized deoxybenzoin.
Figure 4:
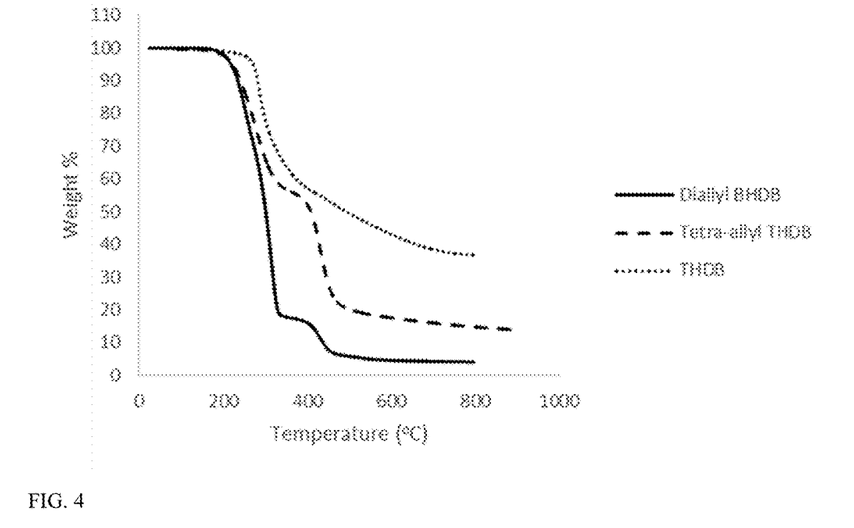
FIG. 4 shows the thermogravimetric analysis of diallyl-functionalized deoxybenzoin ("diallyl BHDB"), tetra-allyl-functionalized deoxybenzoin ("tetra-allyl THDB"), and tetrahydroxydeoxybenzoin ("THDB").
Figure 5:
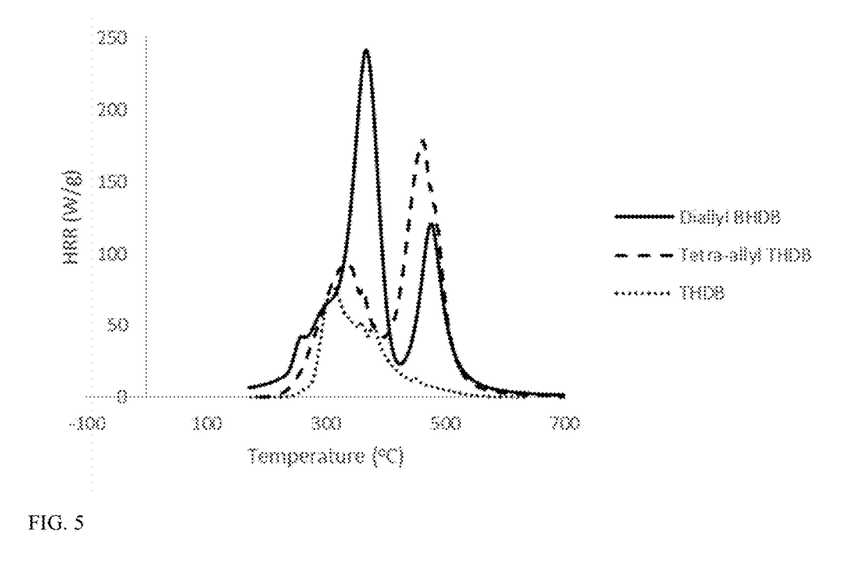
FIG. 5 shows pyrolysis combustion flow calorimetry (PCFC) of diallyl-functionalized deoxybenzoin ("diallyl BHDB"), tetra-allyl-functionalized deoxybenzoin ("tetra-allyl THDB"), and tetrahydroxydeoxybenzoin ("THDB").

The tetra-allyl ether of tetrahydroxydeoxybenzoin (THDB) was prepared according to the following procedure. THDB (15 grams, 57.6 millimoles) was dissolved in acetone (300 milliliters) in a flask, and heat to 60° C. Potassium carbonate (132 grams, 955 millimoles) was added slowly to the solution. The mixture was stirred for 1 hour at 75° C. Allyl bromide (21 milliliters, 243 millimoles) was added via syringe. The reaction mixture was heated to reflux for 24 hours under nitrogen, then allowed to cool to room temperature. Potassium carbonate was removed from the mixture by filtration. The recovered filtrate was diluted with ethyl acetate (500 milliliters) and washed with brine solution. The organic layer was dried over magnesium sulfate, filtered, and solvent was removed under reduced pressure. The dark red crude product was purified by silica column chromatography eluting with hexanes:ethyl acetate (25:75). The tetra-allyl ether of THDB was isolated as a yellow oil (10 grams, 50% yield). The $^1$H NMR spectrum of the tetra-allyl ether of THDB was recorded in dimethylsulfoxide, and is shown in FIG. 3.

The thermal properties of the diallyl ether of BHDB and the tetra-allyl ether of THDB were characterized and compared to the BHDB and THDB starting materials. Heat release capacity (HRC, J/(g-K)), and total heat release (THR, kJ/g) were measured on a microscale combustion calorimeter (MCC). MCC operates as a pyrolysis combustion flow calorimeter (PCFC), and was conducted from 80 to 750° C. at a heating rate of 1° C. per second in an 80 cm$^3$/minute stream of nitrogen. The anaerobic thermal degradation products in the nitrogen gas stream were mixed with a 20 cm$^3$/min stream of oxygen prior to entering the combustion furnace (900° C.). Heat release is quantified by standard oxygen consumption methods typical to PCFC. (See, e.g., Lyon, et al. 2004 J Anal. Appl. Pyrol., 71(1):27-46; ASTM. Standard Test Method for Determining Flammability Characteristics of Plastics and Other Solid Materials Using Microscale Combustion calorimetry. ASTM D7309-13. West Conshohocken, Pa.: ASTM International, 2013, p. 11.) During the test, the heat release rate (HRR) is obtained from dQ/dt at each time interval, taking into account the initial sample mass (~5 milligrams). The HRC is obtained by dividing the maximum HRR by the heating rate. The peak of heat released rate (PHHR, W/g) was obtained by pyrolysis combustion flow calorimeter. Char yields were determined by thermogravimetric analysis (TGA), taken from the mass residue at 750° C. TGA was performed under nitrogen on a Q500 (TA Instruments) at a heating rate of 20° C. per minute. The results are shown in Table 1.

TABLE 1

| Material | HRC (J/g-K) | THR (kJ/g) | PHHR (W/g) | Char Yield (%) |
| --- | --- | --- | --- | --- |
| BHDB | 489 | 26 | 493 | 0 |
| Diallyl-BHDB | 396 | 25 | 238 | 4 |
| THDB | 135 | 9 | 76 | 37 |
| Tetra-allyl-THDB | 248 | 22 | 179 | 15 |

Each of the deoxybenzoin compounds shown in Table 1 showed favorable heat release properties. Diallyl-BHDB shown a reduced HRC compared to BHDB (396 J/g-K compared to 489 J/g-K). The tetraallyl derivative showed increased HRC and THR relative to THDB. Thus, the allyl deoxybenzoin derivatives are expected to be useful for halogen-free flame resistant applications. The thermal characterization of these di and tetra-allyl derivatives of deoxybenzoin reveals low heat release capacities and total heat of combustion, and high char yields. The data obtained by pyrolysis combustion flow calorimetry (PCFC), an oxygen consumption technique, places these novel allyl deoxybenzoin derivatives in the low flammability category despite the absence of any halogens or phosphorus compound in the structure. Advantageous char yields for these materials were also observed. For example, diallyl-BHDB in Table 1 shows a HRC value of 396 J/g-K and a char yield of 4%, while as THDB and tetra-allyl-THDB in Table 1 show a HRC value of 135 and 248 J/g-K, respectively, and high char yields of 37% and 15%, respectively. Having high char yields and low heat release and heat of combustion are desirable properties for flame retardant materials. Furthermore, the absence of undesirable halogens or phosphorus compounds represents another advantage.

The unsaturated deoxybenzoin compounds, polymers prepared therefrom, and articles including the polymer include at least the following embodiments, which are non-limiting.

Embodiment 1: An unsaturated deoxybenzoin compound having the structure (I)

wherein $R^1$ and $R^2$ are independently at each occurrence hydrogen, a halogen, a nitrile group, a $C_{1-6}$ alkyl group, a $C_{2-13}$ alkenyl group, a $C_{2-13}$ alkynyl group, a $C_{6-20}$ aryl group, a $C_{7-13}$ arylalkyl group, or a $C_{7-13}$ alkylaryl group; $R^3$, $R^4$, $R^5$, $R^6$, $R^7$, and $R^8$ are independently at each occurrence hydrogen, a halogen, a hydroxyl group, a nitrile group, a $C_{1-6}$ alkyl group, a $C_{2-13}$ alkenyl group, a $C_{2-13}$ alkynyl group, a $C_{1-6}$ alkoxy group, a $C_{6-20}$ aryl group, a $C_{7-13}$ arylalkyl group, a $C_{7-13}$ alkylaryl group, or a $C_{4-12}$ cycloalkyl group; and n is independently at each occurrence an integer from 1 to 12.

Embodiment 2: The deoxybenzoin compound of embodiment 1, wherein each occurrence of $R^1$ and $R^2$ is hydrogen.

Embodiment 3: The deoxybenzoin compound of embodiment 1 or 2, wherein each occurrence of n is 1.

Embodiment 4: The deoxybenzoin compound of any of embodiments 1 to 3, wherein each occurrence of $R^3$, $R^4$, $R^5$, $R^6$, $R^7$, and $R^8$ is hydrogen.

Embodiment 5: The deoxybenzoin compound of any of embodiments 1 to 4, wherein each occurrence of $R^1$ and $R^2$ is hydrogen; each occurrence of n is 1; and each occurrence of $R^3$, $R^4$, $R^5$, $R^6$, $R^7$, and $R^8$ is hydrogen.

Embodiment 6: The deoxybenzoin compound of any of embodiments 1 to 5, wherein the deoxybenzoin compound exhibits one or more of the following properties: a heat release capacity of less than or equal to 250 joules per gram-Kelvin determined using a pyrolysis combustion flow calorimeter; a total heat release of less than 20 kilojoules per gram determined using a pyrolysis combustion flow calorimeter; a peak heat released rate of less than 200 W/g determined using a pyrolysis combustion flow calorimeter; and a char yield of at least 10 percent after 60 minutes at 750° C., as determined by thermogravimetric analysis.

Embodiment 7: A polymer comprising at least one group derived from a deoxybenzoin compound having structure (I), (II), or a combination thereof wherein $R^1$ and $R^2$ are independently at each occurrence hydrogen, a halogen, a nitrile group, a $C_{1-6}$ alkyl group, a $C_{2-13}$ alkenyl group, a $C_{2-13}$ alkynyl group, a $C_{6-20}$ aryl group, a $C_{7-13}$ arylalkyl group, or a $C_{7-13}$ alkylaryl group; $R^3$, $R^4$, $R^5$, $R^6$, $R^7$, $R^8$, $R^9$, and $R^{10}$ are independently at each occurrence hydrogen, a halogen, a hydroxyl group, a nitrile group, a $C_{1-6}$ alkyl group, a $C_{2-13}$ alkenyl group, a $C_{2-13}$ alkynyl group, a $C_{1-6}$ alkoxy group, a $C_{6-20}$ aryl group, a $C_{7-13}$ arylalkyl group, a $C_{7-13}$ alkylaryl group, or a $C_{4-12}$ cycloalkyl group; and n is independently at each occurrence an integer from 1 to 12.

Embodiment 8: The polymer of embodiment 7, wherein the polymer is derived from the deoxybenzoin compound having structure (I), (II), or a combination thereof, and one or more ethylenically unsaturated monomers.

Embodiment 9: The polymer of embodiment 8, wherein the ethylenically unsaturated monomer is a styrenic monomer, a $C_{1-12}$ alkyl (meth)acrylate monomer, a $C_{6-20}$ aryl (meth)acrylate monomer, a (meth)acrylic acid, an alpha olefin, a vinyl ester, a vinyl alkyl ether, or a combination thereof.

Embodiment 10: The polymer of embodiment 7, wherein the polymer is derived from a polymer having in-chain unsaturation and the deoxybenzoin compound having structure (I), (II), or a combination thereof.

Embodiment 11: The polymer of embodiment 10, wherein the polymer having in-chain unsaturation is an unsaturated polyolefin, an unsaturated aliphatic polyester, an unsaturated elastomer, an unsaturated aliphatic polyurethane, or a combination thereof.

Embodiment 12: The polymer of embodiment 7, wherein the polymer is derived from the deoxybenzoin compound having structure (I), (II), or a combination thereof, and a polymer having one or more unsaturated pendent groups, one or more unsaturated end-groups, or both.

Embodiment 13: The polymer of any of embodiments 7 to 12, wherein each occurrence of $R^1$ and $R^2$ is hydrogen.

Embodiment 14: The polymer of any of embodiments 7 to 13, wherein each occurrence of n is 1.

Embodiment 15: The polymer of any of embodiments 7 to 14, wherein each occurrence of $R^3$, $R^4$, $R^5$, $R^6$, $R^7$, $R^8$, $R^9$, and $R^{10}$ is hydrogen.

Embodiment 16: The polymer of any of embodiments 7 to 15, wherein the polymer comprises at least one group derived from a deoxybenzoin compound having structure (I); each occurrence of $R^1$ and $R^2$ is hydrogen; each occurrence of n is 1; and each occurrence of $R^3$, $R^4$, $R^5$, $R^6$, $R^7$, and $R^8$ is hydrogen.

Embodiment 17: The polymer of any of embodiments 7 to 16, wherein the polymer comprises at least one group derived from a deoxybenzoin compound having structure (II); each occurrence of $R^1$ and $R^2$ is hydrogen; each occurrence of n is 1; and each occurrence of $R^3$, $R^4$, $R^5$, $R^6$, $R^7$, and $R^8$, $R^9$, and $R^{10}$ is hydrogen.

Embodiment 18: The polymer of any of embodiments 7 to 17, wherein the polymer exhibits one or more of the following properties: a char yield of at least 30 percent after 60 minutes at 750° C., as determined by thermogravimetric analysis; a heat release capacity of less than or equal to 250 joules per gram-Kelvin determined using a pyrolysis combustion flow calorimeter; and a total heat release of less than 20 kilojoules per gram determined using a pyrolysis combustion flow calorimeter.

Embodiment 19: The polymer of any of embodiments 7 to 18, wherein the polymer is at least partially crosslinked.

Embodiment 20: An article comprising the polymer of any of embodiments 7 to 19.

Embodiment 21: The article of embodiment 20, wherein the article is a film, a coating, a fiber, a textile, a furniture component, a vehicle component, an electronic component, an adhesive, or a foam.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

All cited patents, patent applications, and other references are incorporated herein by reference in their entirety, including priority application U.S. Patent Application No. 62/316,874, filed Apr. 1, 2016. However, if a term in the present application contradicts or conflicts with a term in the incorporated reference, the term from the present application takes precedence over the conflicting term from the incorporated reference.

All ranges disclosed herein are inclusive of the endpoints, and the endpoints are independently combinable with each other. Each range disclosed herein constitutes a disclosure of any point or sub-range lying within the disclosed range.

The use of the terms "a" and "an" and "the" and similar referents in the context of describing the invention (especially in the context of the following claims) are to be construed to cover both the singular and the plural, unless otherwise indicated herein or clearly contradicted by context. Further, it should further be noted that the terms "first," "second," and the like herein do not denote any order, quantity, or importance, but rather are used to distinguish one element from another. The modifier "about" used in connection with a quantity is inclusive of the stated value and has the meaning dictated by the context (e.g., it includes the degree of error associated with measurement of the particular quantity).

As used herein, the term "alkyl" means a branched or straight chain, saturated, monovalent hydrocarbon group, e.g., methyl, ethyl, i-propyl, and n-butyl. "Alkylene" means a straight or branched chain, saturated, divalent hydrocarbon group (e.g., methylene (—$CH_2$—) or propylene (—$(CH_2)_3$—)). "Alkenyl" and "alkenylene" mean a monovalent or divalent, respectively, straight or branched chain hydrocarbon group having at least one carbon-carbon double bond (e.g., ethenyl (—HC=$CH_2$) or propenylene (—HC($CH_3$)=$CH_2$—). "Alkynyl" means a straight or branched chain, monovalent hydrocarbon group having at least one carbon-carbon triple bond (e.g., ethynyl). "Alkoxy" means an alkyl group linked via an oxygen (i.e., alkyl-O—), for example methoxy, ethoxy, and sec-butyloxy. "Cycloalkyl" and "cycloalkylene" mean a monovalent and divalent cyclic hydrocarbon group, respectively, of the formula —$C_nH_{2n-x}$— and —$C_nH_{2n-2x}$— wherein x is the number of cyclization(s). "Aryl" means a monovalent, monocyclic or polycyclic aromatic group (e.g., phenyl or naphthyl). "Arylene" means a divalent, monocyclic or polycyclic aromatic group (e.g., phenylene or naphthylene). The prefix "halo" means a group or compound including one more halogen (F, Cl, Br, or I) substituents, which can be the same or different. The prefix "hetero" means a group or compound that includes at least one ring member that is a heteroatom (e.g., 1, 2, or 3 heteroatoms, wherein each heteroatom is independently N, O, S, or P.

The invention claimed is:

1. A polymer comprising at least one group derived from a deoxybenzoin compound having structure (I), (II), or a combination thereof wherein $R^1$ and $R^2$ are independently at each occurrence hydrogen, a halogen, a nitrile group, a $C_{1-6}$ alkyl group, a $C_{2-13}$ alkenyl group, a $C_{2-13}$ alkynyl group, a $C_{6-20}$ aryl group, a $C_{7-13}$ arylalkyl group, or a $C_{7-13}$ alkylaryl group;

$R^3$, $R^4$, $R^5$, $R^6$, $R^7$, $R^8$, $R^9$, and $R^{10}$ are independently at each occurrence hydrogen, a halogen, a hydroxyl group, a nitrile group, a $C_{1-6}$ alkyl group, a $C_{2-13}$ alkenyl group, a $C_{2-13}$ alkynyl group, a $C_{1-6}$ alkoxy group, a $C_{6-20}$ aryl group, a $C_{7-13}$ arylalkyl group, a $C_{7-13}$ alkylaryl group, or a $C_{4-12}$ cycloalkyl group; and n is independently at each occurrence an integer from 1 to 12.

2. The polymer of claim 1, wherein the polymer is derived from the deoxybenzoin compound having structure (I), (II), or a combination thereof, and one or more ethylenically unsaturated monomers.

3. The polymer of claim 2, wherein the ethylenically unsaturated monomer is a styrenic monomer, a $C_{1-12}$ alkyl (meth)acrylate monomer, a $C_{6-20}$ aryl (meth)acrylate monomer, a (meth)acrylic acid, an acrylonitrile, an alpha olefin, a vinyl ester, a vinyl alkyl ether, or a combination thereof.

4. The polymer of claim 1, wherein the polymer is derived from a polymer having in-chain unsaturation and the deoxybenzoin compound having structure (I), (II), or a combination thereof.

5. The polymer of claim 4, wherein the polymer having in-chain unsaturation is an unsaturated polyolefin, an unsaturated aliphatic polyester, an unsaturated elastomer, an unsaturated aliphatic polyurethane, or a combination thereof.

6. The polymer of claim 1, wherein the polymer is derived from the deoxybenzoin compound having structure (I), (II), or a combination thereof, and a polymer having one or more unsaturated pendent groups, one or more unsaturated endgroups, or both.

7. The polymer of claim 1, wherein each occurrence of $R^1$ and $R^2$ is hydrogen.

8. The polymer of claim 1, wherein each occurrence of n is 1.

9. The polymer of claim 1, wherein each occurrence of $R^3$, $R^4$, $R^5$, $R^6$, $R^7$, $R^8$, $R^9$, and $R^{10}$ is hydrogen.

10. The polymer of claim 1, wherein
the polymer comprises at least one group derived from a deoxybenzoin compound having structure (I);
each occurrence of $R^1$ and $R^2$ is hydrogen;
each occurrence of n is 1; and
each occurrence of $R^3$, $R^4$, $R^5$, $R^6$, $R^7$, and $R^8$ is hydrogen.

11. The polymer of claim 1, wherein
the polymer comprises at least one group derived from a deoxybenzoin compound having structure (II);
each occurrence of $R^1$ and $R^2$ is hydrogen;
each occurrence of n is 1; and
each occurrence of $R^3$, $R^4$, $R^5$, $R^6$, $R^7$, and $R^8$, $R^9$, and $R^{10}$ is hydrogen.

12. The polymer of claim 1, wherein the polymer exhibits one or more of the following properties:
a char yield of at least 30 percent after 60 minutes at 750° C., as determined by thermogravimetric analysis;
a heat release capacity of less than or equal to 150 joules per gram-Kelvin determined using a pyrolysis combustion flow calorimeter; and
a total heat release of less than 20 kilojoules per gram determined using a pyrolysis combustion flow calorimeter.

13. The polymer of claim 1, wherein the polymer is at least partially crosslinked.

14. An article comprising the polymer of claim 1.

* * * * *